(12) United States Patent
Hartley et al.

(10) Patent No.: US 7,238,198 B2
(45) Date of Patent: Jul. 3, 2007

(54) STENT-GRAFT FASTENING

(75) Inventors: David Ernest Hartley, Subiaco (AU); Edward Graham Mills, Queensland (AU)

(73) Assignees: Cook Incorporated, Bloomington, IN (US); William A. Cook Australia Pty. Ltd., Queensland (AU)

( * ) Notice: Subject to any disclaimer, the term of this patent is extended or adjusted under 35 U.S.C. 154(b) by 485 days.

(21) Appl. No.: 10/602,930

(22) Filed: Jun. 24, 2003

(65) Prior Publication Data
US 2004/0054396 A1    Mar. 18, 2004

Related U.S. Application Data
(60) Provisional application No. 60/391,737, filed on Jun. 26, 2002.

(51) Int. Cl.
*A61F 2/06* (2006.01)
(52) U.S. Cl. ..................... 623/1.13; 623/23.7
(58) Field of Classification Search ...... 623/1.11–1.13, 623/1.23, 1.32, 1.36, 2.17–2.19, 2.38–2.41; 606/232, 233, 151–158
See application file for complete search history.

(56) References Cited

U.S. PATENT DOCUMENTS

| | | | |
|---|---|---|---|
| 4,902,508 A | 2/1990 | Badylak et al. | |
| 5,711,969 A | 1/1998 | Patel et al. | |
| 5,720,776 A | 2/1998 | Chuter et al. | |
| 5,733,325 A * | 3/1998 | Robinson et al. | 623/1.11 |
| 5,733,337 A | 3/1998 | Carr, Jr. et al. | |
| 5,955,110 A | 9/1999 | Patel et al. | |
| 5,968,096 A | 10/1999 | Whitson et al. | |
| 6,004,347 A | 12/1999 | McNamara et al. | |
| 6,206,931 B1 | 3/2001 | Cook et al. | |
| 6,814,748 B1 * | 11/2004 | Baker et al. | 623/1.14 |

* cited by examiner

*Primary Examiner*—David J Isabella
(74) *Attorney, Agent, or Firm*—Richard L. Godlewski

(57) ABSTRACT

A fastening for fixing an exposed stent (2) to a graft material (1). At least two spaced apart fastenings (7, 8) are used, each fastening has at least one turn and preferably two turns of an elongate flexible fiber through the graft material and around a portion of the stent. Each fastening has a knot (9) which is at least two thumb knots and preferably four thumb knots.

12 Claims, 5 Drawing Sheets

STENT-GRAFT FASTENING

CROSS-REFERENCE TO RELATED APPLICATIONS

This application claims priority of provisional application Ser. No. 60/391,737, filed Jun. 26, 2002.

TECHNICAL FIELD

This invention relates to a medical device and, in particular, to a prosthesis or stent graft for use within the human or animal body and, more particularly, to the fastening of a stent to the graft material of the stent graft or prosthesis.

BACKGROUND OF THE INVENTION

Stents are used in association with graft material, for instance, to hold open a tube of graft material and to maintain patency of a lumen. In particular where the stents extend from the graft material either proximally or distally, it is desirable that there is some secure method for fastening of the stent to the graft material.

This invention will be particularly discussed in relation to the fastening of self-expanding stents to polyester graft materials, however, it is to be realized that the invention is not limited to this particular application, but may be applicable to other types of stents and other graft materials.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels corresponding terms such as caudal and cranial should be understood.

SUMMARY OF THE INVENTION

In one form therefore, although this may not necessarily be the only or broadest form, the invention is said to reside in a medical device comprising a graft material and a stent affixed to and extending from the graft material, at least two spaced apart fastenings affixing the stent to the graft material, each fastening including at least one turn of an elongate flexible fibre through the graft material and around a portion of the stent.

Preferably there are two turns of the elongate flexible fibre material through the graft material and around the portion of the stent in each fastening and a knot arrangement which includes at least two thumb knots and preferably four thumb knots to tie off the flexible fibre material.

The flexible fibre material may be a monofilament suture material or braided suture material such as Prolene or Ethebond both sold by Ethicon.

Preferably the graft material is a bio-compatible woven or knitted material such as polyester or polytetrafluoroethylene (PTFE).

The stent may be a balloon expandable stent or a self-expanding stent and in particular may be a self-expanding Z-stent.

Preferably the portion of the stent which is fastened onto the graft material is on the inside of the graft material.

Preferably the knot arrangement is situated on the outside of the graft material thereby not providing a point where thrombus within the graft may occur.

A Z-stent is formed from a plurality of struts with bends in between them and in a preferred form the at least two spaced apart fastenings are placed at the junction of the struts and the bend of a particular apex in a Z-stent or one or more of the fastenings are on the bend. Alternatively, one fastening may be on the bend and another one on one of the struts.

Where one fastening is on the bend and another one on one of the struts adjacent to the bend then the fastening on the strut may be positioned on either strut extending from the bend and at an angle of 50° either side measured around the radius of the bend from the apex.

The at least two fastenings may be spaced apart enough that the turns of fibre do not pass through the same portion of the graft material. The spacing of the at least two fastenings may be from 0.5 mm to 2 mm.

In a further form the invention may be said to reside in a medical device comprising a graft material, a stent having first and second struts and a bend therebetween, a first fastening wrapped around at least one of the first strut, the second strut or the bend and through the graft material, and a second fastening spaced a minimum spacing away from the first fastening and wrapped around at least one of the first struts, the second strut or the bend and through the graft material.

Preferably the fastening may be an elongate flexible fibre or thread such as a mono filament suture material or braided suture material.

Preferably the first and second fastening are wrapped around twice.

Preferably there is a fastening such as a knot arrangement to tie off the flexible fibre or thread which includes at least two thumb knots and preferably four thumb knots.

The at least two fastenings may be spaced apart by from half to two millimetres.

In an alternative attachment arrangement the at least two spaced apart fastenings may be formed from a single length of suture material and spaced apart around the bend of the stent. The attachment may be such that there is a single turn around each stent adjacent a bend and a double turn around the bend itself and then tied off with the knot arrangement.

In a further form the invention may reside in a medical device comprising a graft material, a stent having first and second struts and a bend therebetween, a first fastening wrapped around the first strut and a second fastening wrapped around the second strut, each of the first and second fastenings comprising machine sewn stitches engaging the graft material on either side of the respective struts and passing over the strut.

Preferably there are at least five and more preferably ten machine sewn stitches on each strut.

Preferably the medical device is a stent graft with the stent being an exposed stent extending away from the graft material. The stent may be a self-expanding Z stent which incorporates a plurality of the struts with the bends between adjacent struts.

The graft material may be Dacron, expanded polytetrafluoroethylene (ePTFE), or other synthetic biocompatible materials While Dacron, expanded polytetrafluoroethylene (ePTFE), or other synthetic biocompatible materials can be used to fabricate the coverings for stent grafts, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

DETAILED DESCRIPTION

Figure 1:
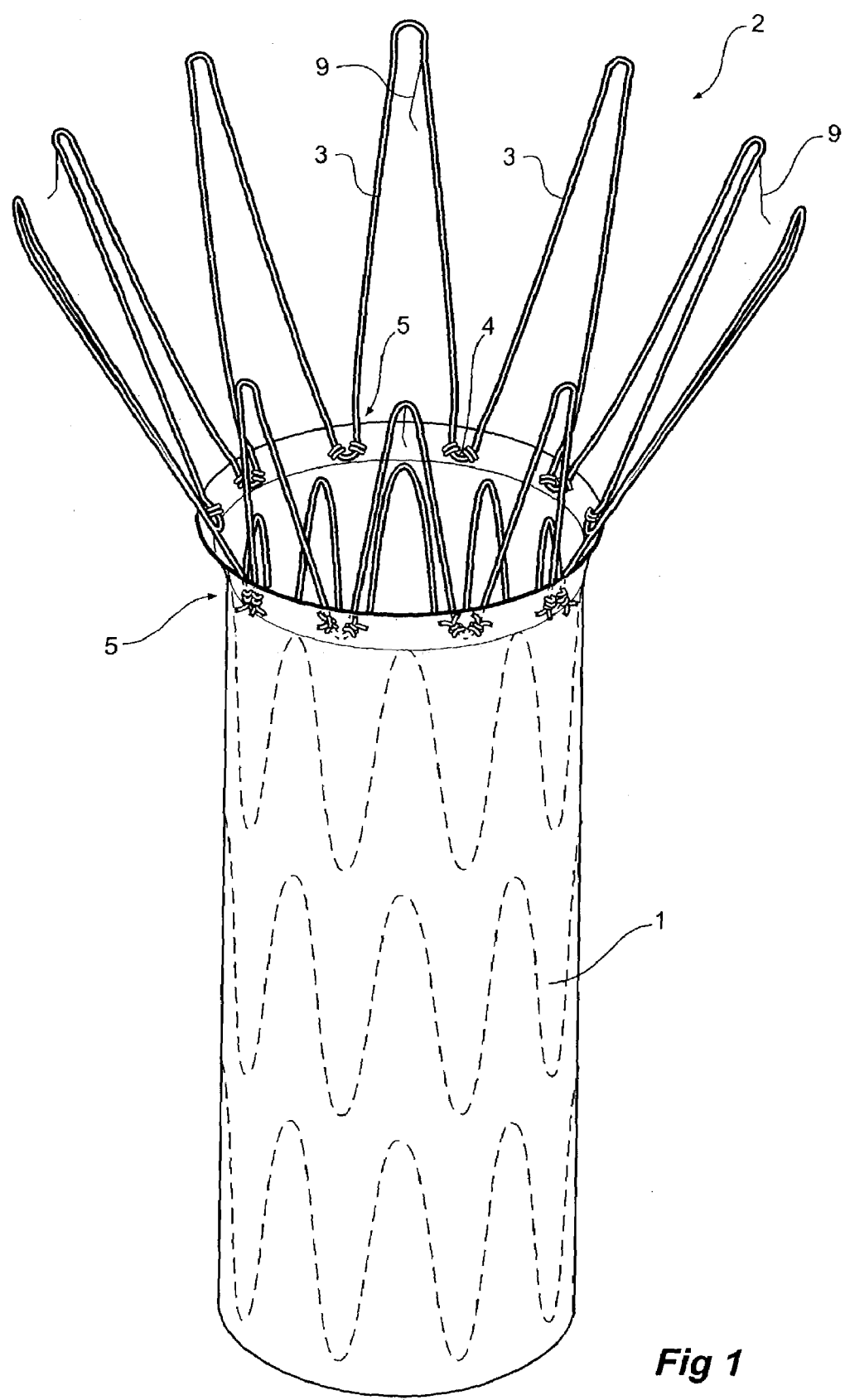
FIG. 1 shows a view of part of one embodiment of a prosthesis or stent graft with a fastening arrangement according to the present invention.

PCT Patent Publication Number WO 98/53761 entitled "A Prosthesis and a Method of Deploying a Prosthesis" discloses an introducer for a prosthesis which retains the prosthesis so that each end can be moved independently. These features and other features disclosed in PCT Patent Publication Number No. WO 98/53761 could be used with the present invention and the disclosure of PCT Patent Publication Number No. WO 98/53761 is herewith incorporated in its entirety into this specification.

PCT Patent Publication Number WO 03/034938 entitled "A Prostheses for Curved Lumens" discloses prostheses with arrangements for bending the prosthesis for placement into curved lumens. This feature and other features disclosed in PCT Patent Publication Number WO 03/034938 could be used with the present invention and the disclosure of PCT Patent Publication Number WO 03/034938 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

U.S. application Ser. No. 10/322,862, entitled "Stent-Graft With Improved Graft Adhesion" discloses arrangements on stent grafts for enhancing the adhesion of such stent grafts into the walls of vessels in which they are deployed. This feature and other features disclosed in U.S. application Ser. No. 10/322,862 can be used with the present invention and the disclosure of U.S. application Ser. No. 10/322,862 is herewith incorporated in its entirety into this specification.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data has shown that the SIS used in, for example, venous valves can be replaced by native tissue in as little as a month's time. In addition to xenogenic biomaterials, such as SIS, autologous tissue can be harvested as well, for use in forming the material. Additionally Elastin or Elastin-Like Polypetides (ELPs) and the like offer potential as a material to fabricate the covering or frame to form a device with exceptional biocompatibility. Another alternative material or tissue would be to use allographs. Such tissue is commercially available in a cryopreserved state.

Figure 2:
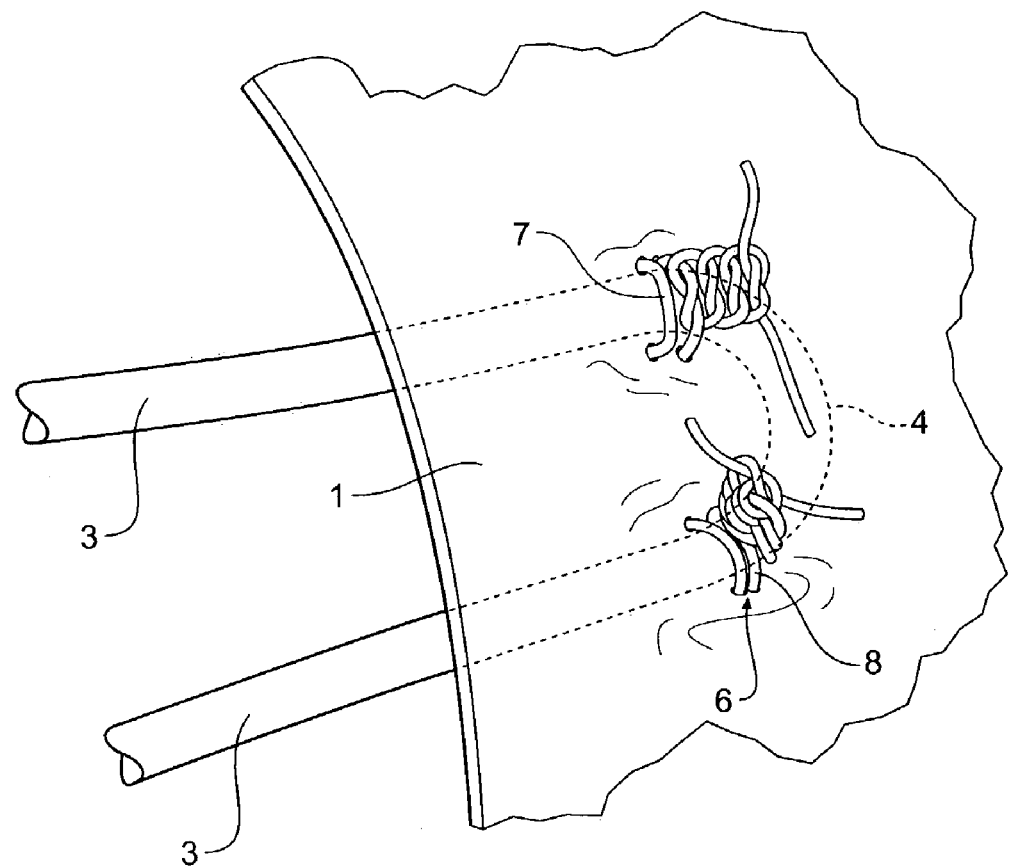
FIG. 2 shows a detail of the fastening of the embodiment shown in FIG. 1.
Figure 3:
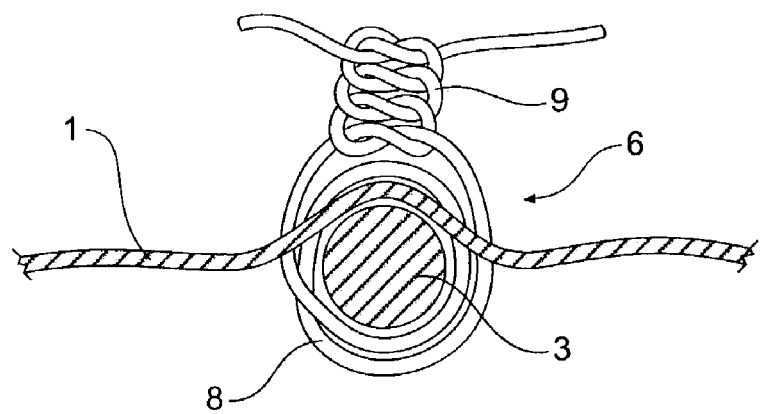
FIG. 3 shows a cross-sectional view of a fastening of the embodiment shown in FIG. 1.

Now looking more closely at the FIGS. 1 to 3 of the drawings, which show a first embodiment of the invention, it will be seen that the prosthesis or stent graft includes a graft material tube 1 with an exposed self-expanding Z stent 2 fastened to and extending from the graft material tube 1. The stent 2 as well as other stents attached to the interior of the graft material tube 1 is composed of a plurality of struts 3 with a bend 4 in between adjacent pairs of struts 3. Some of the struts 3 have barbs 9 which are intended to engage into the wall of a lumen into which it is deployed to prevent movement of the stent in the lumen.

Where the stent graft is deployed in a blood vessel, blood flow causes a pull on the graft material tube which is resisted by the barbs on the stent. Hence the fastenings generally shown as 5 of the stent 2 to the graft material tube 1 takes the pull on the prosthesis and these fastenings must be sufficiently strong to take that pull.

As can be seen in the detailed view in FIG. 2, the struts 3 and bend 4 of the stent passes under or is on the inside of the graft material tube 1, and at least two fastenings 6 and 7 are used to fasten the stent 2 to the graft material tube 1. As shown here, the first and second fastenings 6 and 7 are spaced around the bend adjacent the transition from the bend 4 to the struts of the stent, however, one fastening may be placed on the bend 4 and another on the strut 3 of the stent.

As can be seen in the detailed view in FIG. 3, each fastening 6 and 7 includes at least two turns of a suture material 8 with four thumb knots 9 to tie off the suture material.

Tests have shown that the amount of force necessary to prevent movement of a graft held by barbed stents in an aorta is between 16 to 25 Newtons. This load would normally be taken from the graft material via the fastenings of the stent to the barbs on the stent and as there are between 8 and 12 bends, it can be expected that each fastening may be required to take a load of perhaps 1 to perhaps 5 Newtons. Load can be unbalanced or one barb may take more of the load than others, however, and it is desirable therefore that each fastening should be able to take the entire load with a reasonable safety factor. Each set of fastenings should be able, therefore, to take a force of about 16 to 25 Newtons. Test results to show the strength of various fastening combinations are given below.

Figure 4:
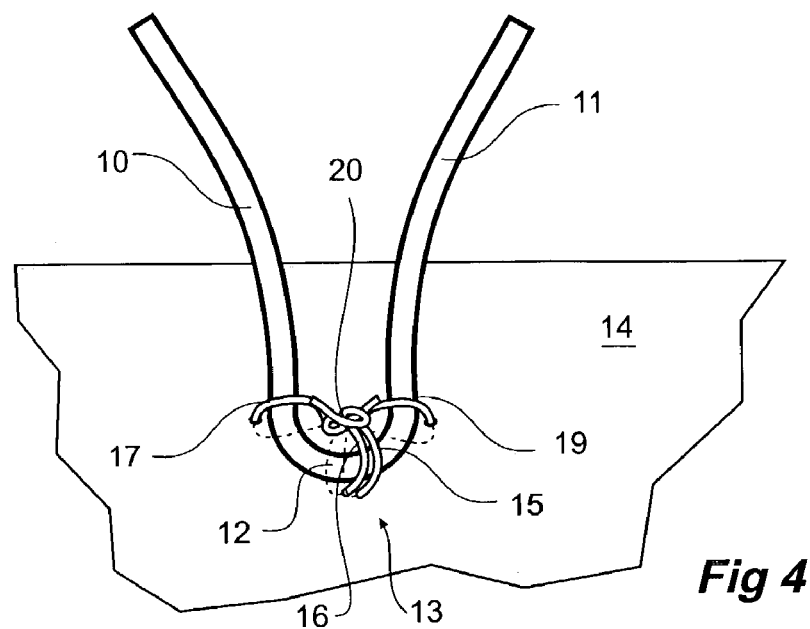
FIG. 4 shows an alternative fastening such as stitching according to the invention.

In the embodiment shown in FIG. 4, the attachment of the stent to the graft material is provided by a single length of suture material in a three lobed stitch.

A portion of the stent including struts 10 and 11 and a bend 12 joining the struts is laid over the graft material 14, and a three lobed stitch generally shown as 13 is formed. The three lobed stitch 13 consists of at least two turns of stitching 15 of a suture thread 16 around the bend 12 and through the graft material 14 and at least one turn of stitching 17, 19 of suture thread 16 around each strut 10 and 11 respectively and through the graft material 14 and then the suture material 16 is tied off with a knot 20 as in the earlier embodiments. The knot 20 knot arrangement to tie off the suture material includes at least two thumb knots and preferably four thumb knots in the suture thread 16. By this arrangement the effect of two spaced apart fastenings is obtained.

Figure 5:
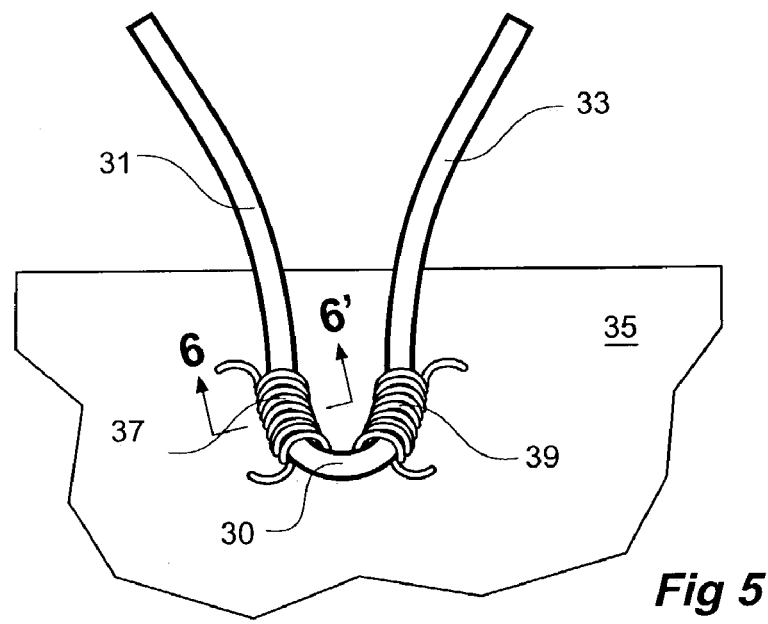
FIG. 5 shows a still further embodiment of stitching according to the invention.
Figure 6:
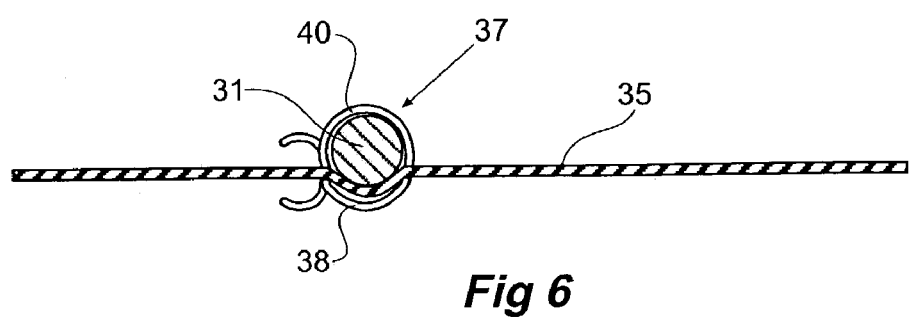
FIG. 6 shows the embodiment of FIG. 5 in cross-section along the line 6–6' in FIG. 5.
Figure 7:
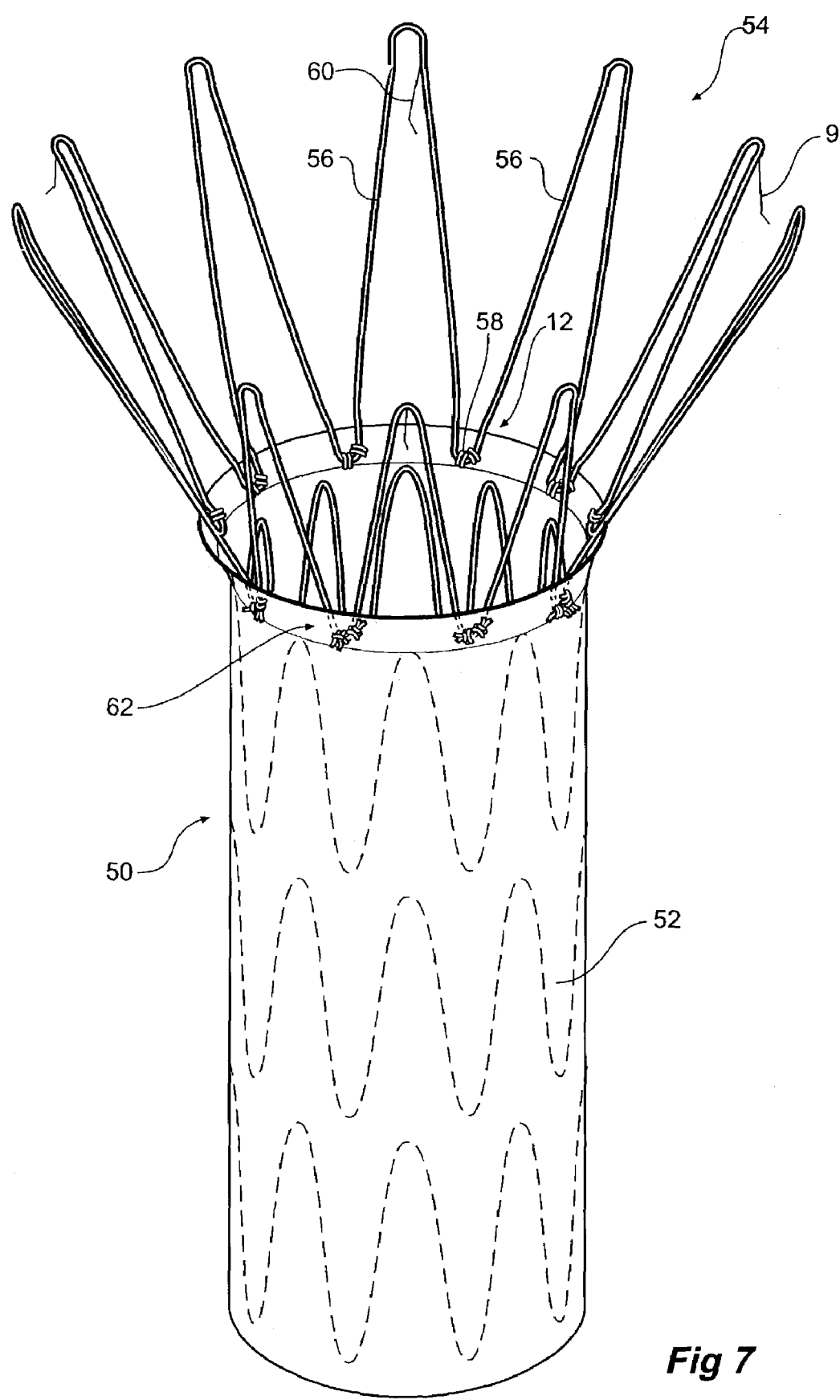
FIG. 7 shows a view of part of a prosthesis or stent graft with a fastening according to an alternative embodiment of the present invention.

In the embodiment shown in FIGS. 5 and 6, the part of the stent incorporating a bend 30 and struts 31 and 33 on either side of the bend is laid over the graft material 35, and a line of stitching 37 and 39 is placed over and along a portion of each strut. Each line of stitching 37 and 39 is a machine formed loop stitching using one strand of thread such as suture material 38 underneath and one strand of thread such as suture material 40 over the top and engaging through the graft material 35 and with each other on each side of the stent 31 (see FIG. 6). This style of stitching may also be referred to as buttonhole stitching. At least five and preferably ten or more stitches may be used on each strut and it may not be necessary to tie off the stitches at each end of the line of stitches as they can be sewn tightly and will not tend to unravel.

FIGS. 7 to 10 show a further embodiment of the invention.

In this embodiment the prosthesis or stent graft 50 includes a graft material tube 52 with a self-expanding Z stent 54 fastened around the periphery of and to and extending from the graft material tube 52. The stent 54 is composed of a plurality of struts 56 with bends 58 in between adjacent pairs of struts 56. Some of the struts 56 have barbs 60 extending from them which are intended to engage into the wall of a lumen into which it is deployed to prevent movement of the stent in the lumen.

Where the stent graft is deployed in a blood vessel, blood flow causes a pull on the graft material tube which is resisted by the barbs 60 on the stent 54. Hence the fastenings generally shown as 62 of the stent 54 to the graft material tube 52 takes the pull on the prosthesis and these fastenings must be sufficiently strong to take that pull.

Figure 8:
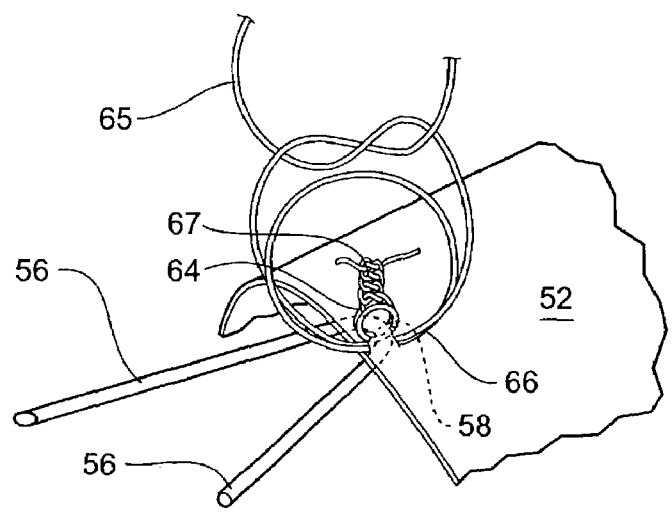
FIG. 8 shows a detail of the fastening of the embodiment shown in FIG. 7.
Figure 9:
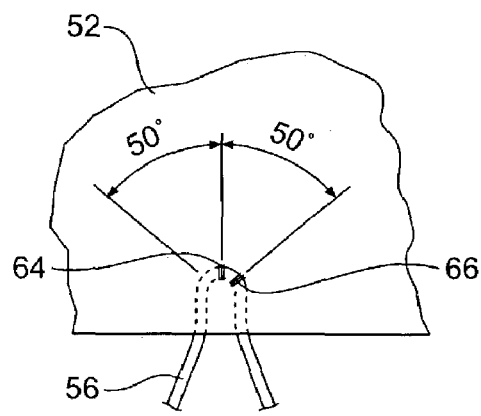
FIG. 9 shows further detail of placement of a fastening of the embodiment shown in FIG. 7.

As can be seen in the detailed views in FIG. 8, the struts 56 and bend 58 of the stent pass under or are on the inside of the graft material tube 52. At least two fastenings 64 and 66 are used to fasten the stent 54 to the graft material tube 52. As shown here, the first fastening 64 is positioned at the apex of the bend 58 and a second fastening 66 is positioned spaced apart adjacent the transition from the bend 58 to the struts 56 of the stent. The second fastening 66, as shown in FIG. 9, can be positioned on either strut 56 extending from the bend 58 in a region extending up to an angle of 50° either side of the first fastening 64 measured around the radius of the bend from the apex of the bend 58. Generally the second fastening 66 is spaced from the first fastening 64 by 0.5 to 2 mm.

Figure 10:
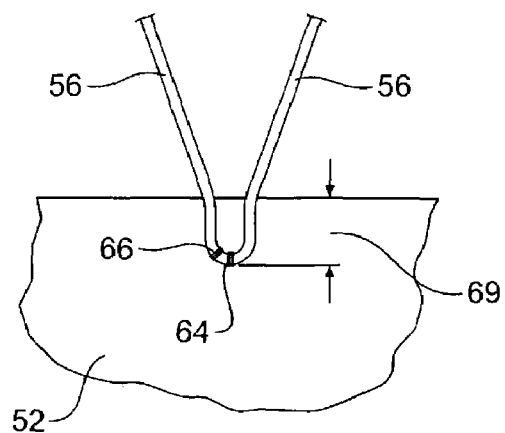
FIG. 10 shows detail of the final placement of a fastening of the embodiment shown in FIG. 7.

The struts and bend of the stent 54 preferably extend over the graft material by a distance of from 2 to 3 mm as indicated by the dimension 69 in FIG. 10.

As can be seen in the detailed view in FIG. 8, each fastening 64 and 66 includes at least two turns of a suture material 65 with between two to four thumb knots 67 to tie off the suture material.

Testing

Test 1

Applicant has performed tests to determine the fastening strength of a nitinol or stainless steel Z-stent into Dacron material using a monofilament suture material.

It should be noted that the direct pull test carried out may not be an entire indication of the strength of a fastening because many factors such as tension of knots causing reduction in cross-sectional thickness of the suture material and movement during use causing wear are not taken into account but the values may be considered to be indicative of the strength of the fastening.

Using Prolene 5.0 (a polypropylene monofilament suture material) as a fastening material the following results shown in Table 1 for a direct pull to failure were obtained.

TABLE 1

| FASTENING CONFIGURATION | RESULTS |
| --- | --- |
| Single Turn/Single Fastening | 10–15 Newtons |
| Two Turns/Single Fastening | 20–25 Newtons |
| Three Turns/Single Fastening | 20–25 Newtons |
| Two Turns/Two Fastenings | 35 Newtons |

As discussed earlier it is estimated that a strength of from 16 to 25 Newtons might be expected to be sufficient to retain a stent to graft material with stitching in use. It will be seen with these test results that a single turn does not give sufficient strength and that three turns in a single fastening are no more effective than two turns. A single turn each in two fastenings gives adequate strength and two turns each in two fastenings gives more than adequate strength.

Using Prolene 4.0, a thicker suture material, as the fastening thread material, the following results as set out in Table 2 were obtained.

TABLE 2

| FASTENING CONFIGURATION | RESULTS |
| --- | --- |
| Single Turn/Single Fastening | 17 Newtons |
| Two Turns/Single Fastening | 20 Newtons |
| Three Turns/Single Fastening | 23 Newtons |
| Two Turns/Two Fastenings | 33–37 Newtons |

It will be seen that the use of two turns gives an adequate result and using two such fastenings gives a superior result. Again, there does not appear to be any significant advantage in providing three turns in a fastening.

The form of stitching shown in FIG. 4 has been tested and has a test strength of about 40–50 Newtons.

The form of stitching shown in FIGS. 5 and 6 has been tested and has a test strength of about 80 to 100 Newtons.

Test 2

Blood flow through the aorta causes a pulsating load upon a stent graft and hence a cyclic fatigue test is useful to determine the long term effectiveness of fastening of stents onto a stent graft. A test was carried out to determine the comparative resistance of single and double loop or turn stent attachments to fatigue.

Each test article was loaded onto an EnduraTEC (Minnetonka, Minn.) longitudinal fatigue tester by attaching the suprarenal stent to the stationary fixture of the tester and the graft body to the moving fixture of the tester and hence putting the fatigue load entirely on the sutures attaching the suprarenal Z-stent. The test article was then subjected to load controlled longitudinal fatigue ranging from 5.0 N to 50.0N in 37° C. distilled water. Each test article was visually monitored periodically and if suture failure occurred, the number of cycles at failure was recorded. If suture failure did not occur, the test was stopped after "runout" of 24 million cycles. The test results for the single and double sutures are summarized in Table 3. The single suture test articles had failures in respective test samples of 10 out of 10 sutures, 8 out of 10 sutures and 8 out of 10 sutures.

Results of the testing are recorded showing the total number of cycles at failure. The data analysis included calculating the means and standard deviations of the number of cycles at suture failure.

TABLE 3

| Description | Quantity | Cycles at Failure |
|---|---|---|
| Single sutured Zenith AAA stent grafts[1] | | |
| Test 1 | 1 | 1,207,526 |
| Test 2 | 1 | 5,715,987 |
| Test 3 | 1 | 3,963,267 |
| Mean ± SD | | 3,628,927 ± 2,272,750 |
| Double sutured Zenith AAA stent grafts[2] | | |
| Test 4 | 1 | Runout (>24 Million) No failure |
| Test 5 | 1 | Runout (>24 Million) No failure |
| Test 6 | 1 | Runout (>24 Million) No failure |

[1] One double-loop suture with four locking knots at each suprarenal stent attachment site (10 sutures total per sample).
[2] Two double-loop sutures with four locking knots at each suprarenal stent attachment site (20 sutures total per sample).

It is clear from this result that two double-loop sutures with four locking knots at each suprarenal stent attachment site provides considerably better fatigue resistance.

Throughout this specification various indications have been given as to the scope of the invention but the invention is not limited to any one of these but may reside in two or more of these combined together. The examples are given for illustration only and not for limitation.

What is claimed is:

1. A medical device comprising: a graft material, an exposed stent affixed to and extending from the graft material, the stent comprising a plurality of struts and bends between adjacent pairs of struts, the bends defining apices, and at least two spaced apart fastenings affixing the stent to the graft material at each apex, each fastening including at least two turns of an elongate flexible fibre through the graft material and around a portion of the stent wherein a first of the at least two spaced apart fastenings is placed at the apex and a second of the at least two spaced apart fastenings is placed adjacent the transition from the bend to the strut.

2. A medical device as in claim 1 wherein the at least two fastenings each include a knot arrangement to tie off the elongate flexible fibre.

3. A medical device as in claim 2 wherein the knot arrangement includes at least two thumb knots and preferably four thumb knots.

4. A medical device as in claim 2 wherein the knot arrangement is situated on the outside of the graft material.

5. A medical device as in claim 1 wherein the flexible fibre is selected from the group comprising a mono-filament suture material and a braided suture material.

6. A medical device as in claim 1 wherein the graft material is a bio-compatible woven or knitted material selected from the group comprising polyester and expanded polytetrafluoroethylene.

7. A medical device as in claim 1 wherein the stent is selected from the group comprising a balloon expandable stent or self-expanding stent.

8. A medical device as in claim 1 wherein the stent is a self-expanding Z-stent.

9. A medical device as in claim 1 wherein the fastenings are spaced apart enough that the turns of fibre do not pass through the same portion of the graft material.

10. A medical device as in claim 1 wherein the spacing apart is from 0.5 mm to 2 mm.

11. A medical device as in claim 1 wherein the least two spaced apart fastenings affixing the stent to the graft material comprise machine sewn stitches engaging the graft material either side of the respective struts and passing over the strut.

12. A medical device as in claim 11 wherein there are at least five stitches on each strut.

* * * * *